(12) United States Patent
à Brassard

(10) Patent No.: US 7,384,559 B2
(45) Date of Patent: Jun. 10, 2008

(54) DEVICE AND METHOD FOR TREATING MAGNETIC PARTICLES

(75) Inventor: Lothar à Brassard, Heinsberg (DE)

(73) Assignee: Chemagen Biopolymer-Technologie AG, Baesweiler (DE)

( * ) Notice: Subject to any disclaimer, the term of this patent is extended or adjusted under 35 U.S.C. 154(b) by 469 days.

(21) Appl. No.: 10/496,062

(22) PCT Filed: Nov. 7, 2002

(86) PCT No.: PCT/EP02/12411

§ 371 (c)(1),
(2), (4) Date: Sep. 7, 2004

(87) PCT Pub. No.: WO03/044537

PCT Pub. Date: May 30, 2003

(65) Prior Publication Data

US 2005/0013741 A1    Jan. 20, 2005

(30) Foreign Application Priority Data

Nov. 19, 2001 (DE) ............................... 101 56 790

(51) Int. Cl.
*B03C 1/00* (2006.01)
*G01N 35/00* (2006.01)

(52) U.S. Cl. .................. 210/695; 210/222; 209/217; 209/232; 435/173.9; 436/526

(58) Field of Classification Search ................ 210/222, 210/695; 209/217, 232; 435/173.9; 436/526
See application file for complete search history.

(56) References Cited

U.S. PATENT DOCUMENTS

| 5,705,062 | A | | 1/1998 | Knobel |
| 5,976,369 | A | * | 11/1999 | Howe et al. ................ 210/222 |
| 6,033,574 | A | * | 3/2000 | Siddiqi ....................... 210/695 |
| 6,150,182 | A | | 11/2000 | Cassaday |
| 6,187,270 | B1 | | 2/2001 | Schmitt et al. |

FOREIGN PATENT DOCUMENTS

| DE | 100 63 984 | 6/2002 |
| EP | 0 589 636 | 3/1994 |
| EP | 0 905 520 | 3/1999 |

* cited by examiner

*Primary Examiner*—David A Reifsnyder
(74) *Attorney, Agent, or Firm*—D. Peter Hochberg; Sean F. Mellino; Daniel J. Smola

(57) ABSTRACT

A device for treating magnetizable or magnetically attractable particles which are present in a liquid, comprising a holder for one ore more reaction vessel(s) with the liquid containing the particles, at least two movably arranged permanent magnets, a drive unit for moving the permanent magnets; with the permanent magnets being arranged in pairs and opposite each other, and being movable in vertical direction (a, b), and the distance between the two permanent magnets of a pair being dimensioned or adjustable such that a reaction vessel can be positioned therebetween.

21 Claims, 2 Drawing Sheets

DEVICE AND METHOD FOR TREATING MAGNETIC PARTICLES

CROSS REFERENCE TO RELATED APPLICATION

This application is a National Stage application of International Application No. PCT/EP02/12411, filed Nov. 7, 2002, which claims priority of German Application No. 101 56 790.1, filed Nov. 19, 2001.

FIELD OF THE INVENTION

The invention relates to devices and methods for treating magnetizable or magnetically attractable particles (magnetic particles). More particularly, it relates to magnetic particles having specific binding properties for certain substances and used for separating these substances from complex mixtures.

DESCRIPTION OF THE PRIOR ART

The method of separating substances utilizing magnetic particles has a great variety of uses since such magnetic particles can be equipped with most different binding properties. They can be used, for example, for sequence-specific isolation of nucleic acids or in immunological assays based on antigen-antibody binding.

Methods based on magnetic separation using specifically binding magnetically attractable particles are increasingly gaining in significance in the field of samples preparation for diagnostic or analytical examinations. This is true, in particular, for automated processes, since it is thereby possible to analyse a large number of samples within a short period of time. This creates the conditions for an efficient screening with high sample throughput. This is of enormous significance, for example, for applications in molecular-genetic studies or in the field of genetic diagnostics as it is practically impossible to cope with very large numbers of samples with purely manual handling.

The basic principle of magnetic separation of substances from complex mixtures is conceivably simple. Magnetic particles (magnetizable or magnetically attractable particles) are functionalised in a specific manner for the intended separation process, i.e. they are provided, by chemical treatment, with specific binding properties for the target substances to be separated. For certain frequently occurring application purposes, such functionalised magnetic particles are also commercially available. The size of such magnetic particles generally is in the range of about 0.05 to 500 µm.

In a first step ("binding step") of the known separation process, the aforementioned functionalised magnetic particles are added in a reaction vessel to a (starting) mixture which is to be purified and which contains the target substance(s) in a liquid promoting the binding of the target substance molecules to the magnetic particles (binding puffer or binding liquid). This causes a selective binding of the target substance(s) present in the mixture to the magnetic particle(s) (=binding step). Since the binding reaction is time-dependent, the binding step must be carried out over a certain period of time to achieve a binding of the target substance molecules present to the magnetic particles. Problematic in this connection is the fact that the magnetic particles tend to sediment due to the gravimetric forces. This impairs the efficiency of the binding of target group molecules to the magnetic particles, especially owing to the limited diffusion.

Subsequently, these magnetic particles are immobilised (reversibly) on a site of the interior wall of the reaction vessel by employing magnetic forces or a magnetic field, for instance by means of a permanent magnet, where as a rule they form a "pellet".

Thereafter, the liquid supernatant is separated and discarded, for example, by suction or decanting. Since the magnetic particles are immobilised in the manner described, it is largely prevented that these particles are separated along with the supernatant.

This binding step is generally followed by one (or several) washing step(s), wherein the pellet of the magnetic particles is resuspended in a suitable wash liquid and mixed therewith. The wash liquid and the conditions of the washing are selected such that the specific binding of the target substance to the magnetic particles is not impaired. In this way, by means of the washing, a separation of unspecifically bound substances is brought about and the purity of the target substances to be separated is ultimately increased. As described before with reference to the binding steps, after the washing step(s), too, the supernatant (i.e. the wash liquid) is separated and discarded following the immobilizing of the magnetic particles.

In the elution step following the wash step(s), the magnetic particles immobilized as a pellet are again resuspended. To this end, an elution liquid or elution buffer is used which is suited for breaking the bond between the target substance(s) and the magnetic particles, so that the target substance molecules can be released from the magnetic particles and separated along with the elution liquid. During separation of the elution liquid, the magnetic particles are immobilised as described above.

The compositions of the binding, wash and elution liquids used in these separation methods are known to those skilled in the art, or they can be elucidated for an individual case by means of preliminary tests.

The process of resuspending of the immobilised magnetic particles (magnetic particle pellet) has a decisive influence on the purity and yield of the target substances to be separated (the separation product).

If the magnetic particles are only insufficiently resuspended during washing, and agglomerates of particles remain, the washing is as a consequence rendered insufficient and the intended separation of unspecifically bound impurities takes place to an insufficient degree or not at all. In that case, the purity of the separated target substances, that is, the separation product is of poorer quality.

If, during the elution step, the magnetic particles are not completely or only insufficiently resuspended, this leads to the elution taking place only insufficiently, so that only part of the target substances bound to the magnetic particles becomes detached from the particles, while another part remains bound thereto and does not pass over into the elution liquid. The yield is thereby more or less reduced, which is of disadvantage particularly in those cases where the target substances to be separated are present in the starting mixture examined only in very small concentrations.

It is especially unfavourable if as a result of insufficient resuspending during the washing and during elution, both the purity and the yield of the product to be separated are reduced.

The process of resuspending is problematic particularly if the above described sequence of the separating process is carried out by means of automated devices which are to enable a high sample throughput.

Resuspending is additionally made difficult by the fact that the sample volumes and the reaction vessels used are very small (miniaturisation). In addition, resuspension is to take place within a period which is to be as short as possible in order to ensure high sample throughput.

Resuspending can be brought about, for example, by repeatedly pipetting on and off of the liquid present above the magnetic particle pellet until the pellet disintegrates and the particles have been distributed in the liquid. However, for this process, additional single-use pipette teats are used up, which in view of the large sample numbers leads to considerable additional costs.

Another known possibility consists of immersing moving (e.g. rotating) stirrers, such as permanent magnet rods, into the reaction vessels and in this way to bring about a disintegration of the pellets, and a mixing and resuspension. For very small sample volumes, as used in high-throughput screening processes, this method of resuspending is only partly suitable since the submerged stirrer requires additional space. Moreover, the dipping and subsequent taking out of the said stirrers can lead to losses of sample material or to contamination unless suitable countermeasures are taken.

In addition, resuspension can be affected in a known manner by vibrating or by means of a shaking device. This, however, has the disadvantage that it necessitates additional apparatuses (cost factor) and that the process requires additional operation steps and time, for instance for inserting the samples into the shaking device and thereafter taking them out again. Moreover, this method is little suited, in particular, where very small reaction volumes are involved, for example for resuspending a pellet of magnetic particles.

SUMMARY OF THE INVENTION

The task of this invention was therefore to provide devices and processes for treating magnetic particles which in the magnetic separation processes of the kind described enable a more efficient and more rapid resuspension of the pelletised or immobilised magnetic particles, especially in the washing and elution steps, and which enable a more efficient realisation of the binding step, whereby the above-mentioned disadvantages as well as other disadvantages of the known methods are to be avoided.

The solution of this task is made possible by the devices of the present invention as well as by the processes of the present invention, and by the preferred embodiments of said devices and processes as described herein.

The invention will in the following be explained with reference to the schematic representations shown in FIGS. 1 and 2. These drawings are merely to illustrate the functional principle and are by no means to be understood as restricting the invention to the embodiments represented.

DETAILED DESCRIPTION OF THE INVENTION

Figure 1:
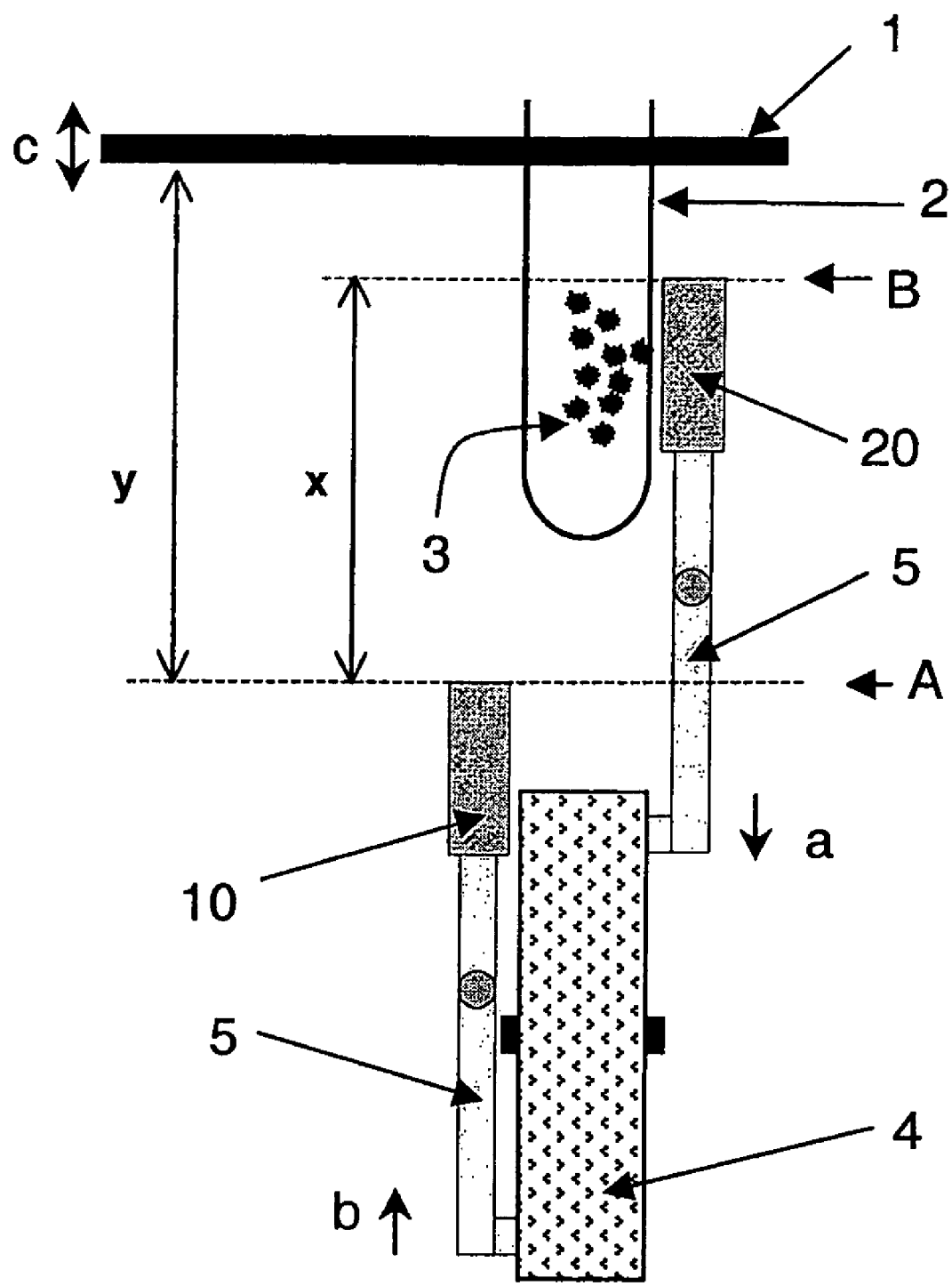
FIG. 1 and FIG. 2 each show a schematic (longitudinal) sectional representation of the device according to the present invention.

According to the present invention, a device for treating magnetisable or magnetically attractable particles 3 which are present in a liquid comprises a holder 1 for one or more reaction vessel(s) 2 with the liquid containing the particles 3, at least two movably arranged permanent magnets 10, 20, as well as a drive unit 4 for moving the permanent magnets 10, 20.

The permanent magnets 10, 20 are arranged in pairs and opposite one another, and movable downwards and upwards in a vertical direction (arrows a, b).

The distance between the two permanent magnets 10, 20 of a pair is selected or adjustable such that a reaction vessel 2 can be positioned between them. The mentioned "opposite arrangement" also encompasses such arrangements where the magnets are not exactly opposing each other in one line (180°); rather, this angle may also be less than 180° (about 180° to about 120°), or the two permanent magnets may be arranged laterally offset from each other, relative to the reaction vessel positioned between them.

Figure 2:
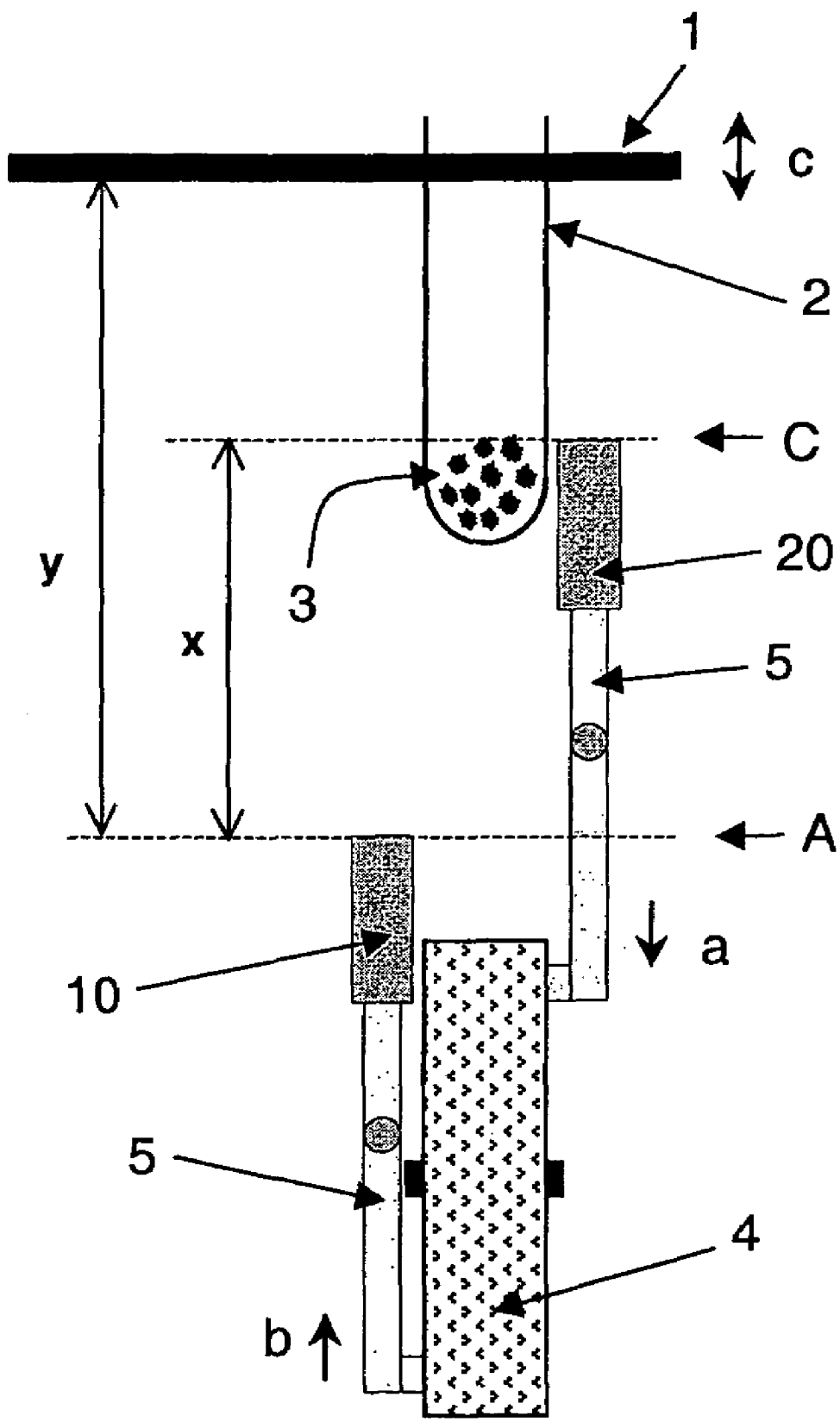

The devices are arranged or controllable such that the described movement of the permanent magnets 10, 20 takes place in such a way that each permanent magnet of a paired arrangement can be brought from a first position or start position (A), in which it is at a distance from the reaction vessel and exerts essentially no influence on the mentioned particles 3 (magnet 10 in FIGS. 1 and 2), to a second or another position (work position) (B, C), in which it is located laterally next to the reaction vessel 2 concerned and exerts a magnetic force on the particles 3 (magnet 20 in FIGS. 1 and 2). The distance x between the two positions (A, B; dashed line in FIGS. 1 and 2) is adjusted such that the magnetic force of the magnet located below (position A), due to the special distance, no longer has any effect on the particles present in the reaction vessel.

The vertical position of the work position (B) can be changed or pre-determined, for instance depending on the length of the utilized reaction vessels 2 or on the volume of the liquid in the reaction vessel.

The lateral distance between a permanent magnet in work position and the reaction vessel to be treated is kept as small as possible so that only a small gap of preferably less than 5 mm, in particular less than 2 mm, remains.

Furthermore, the device is adjusted or programmed such that the two permanent magnets 10, 20 of a pair-wise arrangement, alternating with each other, take up the above-mentioned first position (A) or the above-mentioned work position (B) or (C), relative to the reaction vessel 2 positioned between the magnets, while alternating between the said positions at a predeterminable speed and for a predeterminable duration.

By the quickly alternating positioning of a magnet on opposite sides of the reaction vessel, which is made possible by this invention, the magnetic particles initially present in a pellet (not shown in FIG. 1) are torn apart quickly and efficiently and are resuspended after only a few cycles of magnet alternation. This effect would not occur, or would occur only after a considerably longer period of time, if only one magnet were moved from one side of the reaction vessel to the other (for example, by pulling the magnet from one side to the other underneath the reaction vessel), since, as experience shows, this would lead to the pellet as a whole (i.e. without disintegrating) being pulled across the bottom of the reaction vessel. This would involve loss of yield, increased time-expenditure for the processing and reduced purity of the separation product.

The devices according to the present invention can be adapted according to requirements in such a way that they are optimally suited for larger sample volumes (e.g. in the millilitre range) or for smaller sample volumes (e.g. in the microliter range).

The holder 1 may optionally be configured such that it is suitable for receiving individual reaction vessels, e.g. cuvettes or Eppendorf vessels, or for receiving microtitre plates having a plurality of wells. Further, the holder 1 may be mounted such that it can be moved in the horizontal plane in at least one direction, preferably automatically or programme-controlled, for example in order to bring a reaction vessel 2 into the position between the permanent magnets 10, 20, or to transport it further in order to perform a further treatment step.

The individual, above-described elements of the devices according to the present invention may also be realised such that a plurality of said elements is present in one device. Furthermore, in a further embodiment, several of the arrangements of movable permanent magnets shown in FIG. 1 are positioned in a row, so that simultaneous treatment of a row of reaction vessels placed side by side is made possible. A device for magnetic separation may also comprise several of such rows, each of which containing several arrangements of movable permanent magnets.

In this case, each of the individual arrangements may be activated via its own drive unit, or the multiply present arrangements of movable permanent magnets may be activated via a common drive unit.

The motion of the permanent magnets 10, 20 is effected by one or more drive units 4, possibly using additional means 5 for power transmission. The drive itself can be accomplished by means of electromotors, electromagnets, or by pneumatic or hydraulic means, it also being possible to utilize the said means in combination. The drive may comprise, for instance, a crankshaft, eccentric discs, guide rails, push and pull rod assemblies, or other components known to those skilled in the art, by means of which the motion of the magnets is affected.

As permanent magnets, magnets of suitable shape available in specialist shops may be used, these are preferably NdFeB materials. In the individual case, it may be of advantage to use permanent magnets which are specifically adapted to the shape of the reaction vessels used in each particular case. A permanent magnet may be composed of a plurality of individual magnets; furthermore, a pair-wise arrangement may from case to case also comprise more than two permanent magnets.

Preferably, the two permanent magnets 10, 20 of a pair-wise arrangement may be mechanically coupled with each other in such a way that one magnet is located in the above-mentioned first position (A), relative to the reaction vessel, when the other magnet is in the above-mentioned second or other position (B), and vice versa.

Furthermore, it is preferred for the two permanent magnets 10, 20 of a pair-wise arrangement to be mechanically coupled to each other in a manner such that the vertical directions of movement (a, b) of the pair-wise arranged permanent magnets 10, 20 are opposite to each other.

Instead of the above-mentioned mechanical coupling, one may also use a corresponding circuit or control that has the same effect.

According to a further preferred embodiment, the drive of the movable permanent magnets is programme-controlled. This can be accomplished, preferably, by means of an integrated microprocessor control unit, or by means of a computer connected via an interface. In addition, by means of the said programme control, further functions of the devices according to the invention may be controlled as well, for example the movement of the holder 1 in a horizontal and/or vertical direction, or possibly present pipetting units.

Preferably, the aforementioned programme control is configured such that it predetermines or controls one or more of the following functions or parameters (singly or in combination):

the velocity, and/or the frequency, and/or the number of cycles of the movement of the magnets, and/or the duration of the pause intervals (dwell time) between the movement, and/or the position of the said first or other working position in vertical direction, and/or the sequence in which the permanent magnets take up the above-mentioned different positions.

If an arrangement comprises a plurality of pair-wise magnetic arrangements, e.g. in a row, the sequence of motions of these multiple units is coordinated preferably by means of programme control.

The various parameters, such as velocity of the movement of the permanent magnets, duration or dwell time, number of cycles etc, is dependent, inter alia, on the type of samples to be treated in a particular case, as well as on the kind of the respective treatment step. These parameters can be elucidated and optimized by the skilled artisan by means of simple preliminary tests.

According to a further embodiment, which is especially preferred, at least one of the movable permanent magnets 10, 20 can be brought into a position in which it is beside the reaction vessel 2 in question and at the bottom end thereof and in which it exerts a magnetic force on the particles (position C in FIG. 2, magnet 20). This pre-determined, or pre-determinable, position is called "elution position", since due to the position of the magnets at the bottom end of the reaction vessel a relatively small volume of elution liquid is sufficient to enable the resuspension of the particles in the elution liquid. A small elution volume is desirable in order for the eluted target substance to be obtained at a concentration as high as possible. Conversely, in the wash steps, relatively large volumes of wash liquids are used, which is why in this case the upper position of the permanent magnet is preferably higher, relative to the reaction vessel (see position B in FIG. 1).

Reaching the elution position is made possible by the fact that the holder 1 for the reaction vessels is arranged so as to be movable in vertical direction (arrow c), and by the said holder being positioned in a higher, determined or pre-determinable position, relative to the starting level, during the elution process. This means that by means of the movement of the holder the vertical distance between the holder 1 and the permanent magnet arrangement 10, 20 is made larger (distance y in FIGS. 1 and 2, respectively).

The distance x between the starting position A and the working position B (FIG. 1) or, respectively, the elution position C (FIG. 2) of the permanent magnets preferably remains unaltered in the process.

Alternatively, the permanent magnets may also be brought into an elution position by moving them—the level of the holder 1 preferably remaining constant—into a work position by shortening the distance x, this work position being lower (and thus nearer to the bottom of the reaction vessel) than the above-mentioned work position used during the washing steps and designated in FIG. 1 with B (Magnet 20). In this case, too, the permanent magnet in the elution position is located beside the reaction vessel 2 in question, but at the bottom end thereof.

Another measure by means of which a magnet can be brought into the above-described elution position consists in moving or altering the position of the drive unit 4 (with which the permanent magnets are connected). To this end, the drive unit is arranged such that it may be moved downwards (lowered) in a pre-determined manner and remains in that position during the elution step. By positioning the drive unit in this way, it is achieved that a magnet, when being located in the mentioned upper or working position, gets to lie in the vicinity of the bottom end of the reaction vessel. In this case, too, the distance y, respectively the vertical distance between the drive unit and the bottom end of the reaction vessel, is enlarged.

The latter embodiment of the device described above, wherein the relative position of the drive unit is alterable, is of advantage especially in those cases where a vertical movement of the holder 1 cannot be realised for reasons of space.

According to a preferred embodiment, the direction and/or distance and/or velocity of the movement of the drive unit, respectively the holder, and/or the intermediate pause intervals are predeterminable or programmable.

The movement of the holder, respectively of the drive unit in vertical and/or horizontal direction may be accomplished with means similar to those described with respect to the movement of the permanent magnets (motor, pneumatically, etc.). In that case, too, it is preferred to provide a programme control which enables predetermination and control of the direction and/or distance and/or velocity of the movement, and/or the intermediate pause intervals. A coordination of the movement of the holder, respectively of the drive unit, with the movement(s) of the permanent magnets can be achieved in this way too.

The device according to the invention may, furthermore, be configured such that it provides a further work position which largely corresponds, for example, to the above-mentioned elution position and where at least one of the permanent magnets is capable of exerting an influence on the magnetic particles such that they are immobilized on the inner wall of the reaction vessel, respectively form a pellet there. The device may in this case also be utilized for performing the pelletizing steps of the separation process (e.g. for suction of the washing liquid supematants or of the eluate containing the target substance(s). Depending on the particular application case, it is also possible to select another suitable working position of the magnet(s) for the pelletizing step, such as the above-mentioned working position B in FIG. 1.

The dwell time of the magnet in the mentioned position (for pelletizing/immobilizing) is predeterminable or programmable. During the dwell time, the drive of the magnet(s) is temporarily switched off or interrupted.

The pelletizing/immobilizing step is commonly coordinated or synchronized, by means of a circuit or a programme control, with the step of sucking up the wash liquid or the eluate.

The devices according to the invention may furthermore be utilized to advantage for carrying out the binding step mentioned at the beginning which is used in magnetic separation processes. For this purpose, in the device, provision is made that the movement of the magnets (relative to the reaction vessel being treated) can be adjusted or programmed such that due to this movement the gravimetrically caused sedimentation of the magnetic particles is prevented. This may be achieved, for instance, by a slowed down movement of the magnets.

By preventing the gravimetric sedimentation of the magnetic particles during the binding step the efficiency of the binding of the target substance molecules to the magnetic particles is increased, which in turn results in an improved yield.

According to a preferred embodiment, the devices according to the invention may be provided with means necessary for performing the further operational steps of magnetic separation processes. Among these are, in particular, devices for sucking off liquids from the reaction vessels and/or pipetting devices for metering or suction of defined volumes of liquid to the reaction vessels or from the reaction vessels, respectively. These additional means are preferably also programme-controllable.

The devices according to the present invention may, however, also be mounted as modules in commercial liquid-handling apparatuses, and combined therewith. The liquid-handling apparatus here takes over the procedures of filling the reaction vessels with liquid (e.g. binding, washing or elution liquid) as well as suction or drawing-off of the liquid from the reaction vessels.

In such a combined apparatus, the devices according to the present invention take over one or more of the following processes:
performing the binding step;
resuspending the magnetic particles (e.g. in washing or elution liquid); and
pelletizing or immobilizing the magnetic particles during suction/drawing-off of a liquid.

The device according to the invention and the method for treating magnetic particles underlying the same stand out for excellent resuspending properties, for high efficiency in the binding step, for high purity and high yield of the separation products, for saving of time, as well as for low consumption of consumption materials, such as pipette teats, in performing magnetic separation processes.

Due to the possibility of altering the vertical distance of the magnets (distance x) and/or the vertical distance (distance y) between the magnets and the reaction vessel, respectively the holder 1 and/or the vertical position of the drive unit and/or the horizontal distance between the magnets, the device can be adapted in numerous ways to large reaction volumes or different sizes or shapes of reaction vessels. The simplicity of the system enables a good control of the individual functions, adapted to the respective application.

With the present invention a process for treating a magnetic particle or a plurality of magnetic particles present in a reaction vessel, for instance in the form of a pellet, in order to resuspend said particles in a liquid, e.g. in a washing, elution or binding liquid, will be made available. This is achieved by positioning a permanent magnet in alternating order at opposite sides of the reaction vessel 2, so that it is in each case located next to the reaction vessel in question and exerts a magnetic force on said particles 3. The alternation to and from of the magnet between the two opposite sides leads to the pellet being torn apart and to the magnetic particles in the liquid being suspended.

The present invention further relates to processes for treating magnetizable or magnetically attractable particles which are present in a reaction vessel, e.g. in the form of a pellet, with a liquid, for instance a washing, elution or binding liquid.

These processes comprise the steps: adding a predetermined amount of a liquid to a pellet containing magnetic particles; resuspending the pelletized particles and mixing with the liquid.

According to the invention, step b) is carried out in such a manner that: the above-mentioned vessel 2 is positioned between two permanent magnets 10, 20 which are vertically movable and arranged in a pair and opposite each other, and the above-mentioned movement of the permanent magnet is performed such that each permanent magnet of a paired arrangement is brought from a first position or starting position (A), wherein it is located at a distance from a reaction vessel and wherein it has substantially no influence on the mentioned particles 3, to a second or to another position (B, C) (working position), wherein it is located laterally next to the reaction vessel 2 concerned and wherein it exerts a magnetic force on the particles. Preferably, the magnet remains in this position for a predetermined period of time (dwell time) in each case, before it returns to its starting position.

The two permanent magnets of a paired arrangement alternate with each other in taking up the said first position (A) or the said working position (B, C), relative to the reaction vessel positioned between them, and they alternate between the said positions at a predeterminable velocity and for a predeterminable duration.

By the alternating positioning of the permanent magnets in quick succession at opposite sides of the reaction vessel, a rapid and efficient dissolution of the pellets and resuspension of the magnetic particles is achieved.

The above-described process may also be utilized for carrying out the above-mentioned binding step in magnetic separation processes. Here, the magnetic particle(s) are placed in a reaction vessel which contains the target substance to be separated in a liquid (binding liquid or binding puffer). By means of the described movement of the permanent magnets, the sedimentation of the magnetic particles, which is due to gravitation, can be counteracted, i.e. the particles are maintained during the binding step in a floating or suspended state in the liquid. As a consequence, the efficiency of the binding step is increased and the yield improved.

To be able to carry out the elution step (step b) with an elution volume which is as small as possible—in cases where an elution fluid is used for eluting of substances bound to the particles—one variant of the process is preferred wherein a permanent magnet is located in the working position, i.e. during resuspending, laterally next to the reaction vessel concerned and at the bottom end thereof (elution position C).

This may preferably be achieved by moving the reaction vessel or a holder carrying the reaction vessel in vertical direction, relative to the working position of the permanent magnet, from a lower or starting position into a pre-determinable upper position, as schematically shown in FIG. 2 (Distance y).

Alternatively the same purpose may be achieved—as already mentioned—by altering the position of the drive unit for the magnet in a substantially vertical direction, or by controlling the movement of the permanent magnets such that the upper working position reached in each case gets to lie lower and nearer to the bottom end of the reaction vessel, compared to the working position which is reached during the resuspending process during a wash step.

To make the resuspension process during a washing step or during an elution step more efficient, it may be advantageous if, after the positioning of a magnet in working position, a dwell time starts which lasts approximately until the magnet particle pellet starts to become detached from the wall of the vessel. The next positioning step, i.e. alternating between the starting and working positions of the paired permanent magnets, takes place only after this dwell time. The length of the dwell time as well as the repetition cycles of the positioning processes of the magnets are preferably controlled by means of a computer programme.

The processes mentioned are performed preferably utilizing the devices according to the invention as above-described.

The devices and processes according to the present invention may be employed—while taking advantage of the above-described advantages—in the various separation processes which are based on magnetically attractable microparticles. Due to the more efficient, quicker resuspension it is possible with the invention to achieve—in particular in high-throughput processes—an increase in performance and cost-saving.

DESCRIPTION OF THE FIGURES

FIG. 1 shows, in section, the schematic structure of a device according to the invention, comprising a holder 1 for reaction vessels 2, which holder can be moved upwards and downwards in the direction of the arrow c. The holder is located substantially in a horizontal plane relative to the direction of motion of the permanent magnets. The holder may be arranged such that it is movable within the horizontal plane in one, two or more directions.

The reaction vessel 2 contains magnetically attractable or magnetizable particles (magnetic particles) 3, usually suspended in a liquid.

Below the reaction vessel there is a unit of permanent magnets 10, 20 arranged in a pair, between which a reaction vessel 2 is arranged. The magnets are alternately moved, by means of a drive unit 4 and drive elements associated therewith 5, in vertical direction in the direction of the arrows a and b, respectively, with each magnet alternating between a starting position (A) and (B), respectively. In the case represented, the magnet 10 is located at the starting position (A) and the magnet 20 in the working position (B). In the working position, the respective magnet is located next to the reaction vessel, so that it is able to exert a magnetic force on the particles suspended in the vessel.

Arrow x designates the distance between the starting position and the working position of the two permanent magnets.

Arrow y designates the distance between the starting position (A) of the permanent magnets and the holder 1 for the reaction vessels.

FIG. 2 corresponds to FIG. 1, with the exception that the holder 1 has been moved vertically upwards, so that the distance y is larger.

As a consequence, the permanent magnet 20, when being located in its working position C, gets to lie near the bottom end of the reaction vessel. This position (relative to the reaction vessel) is called elution position.

The position of the starting position A and the length of the distance x is the same as in FIG. 1.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

I claim:

1. A device for treating magnetizable or magnetically attractable particles which are present in a liquid, comprising:
    a holder for holding at least one reaction vessel with the liquid containing the particles;
    at least two movably arranged permanent magnets;
    a drive unit for moving the permanent magnets;
    said permanent magnets being arranged in pairs and opposite to each other, and being movable linearly in a vertical direction relative to the level of said liquid in the at least one reaction vessel;

the distance between the two permanent magnets of a pair being dimensioned or adjustable such that a reaction vessel of said at least one reaction vessel can be positioned therebetween;

the movement of the permanent magnets taking place so that each permanent magnet of said paired arrangement being alternately brought from a first position or start position, in which said permanent magnet is at a distance from one vessel of the at least one reaction vessel and said permanent magnet having essentially no influence on the particles, to a second or other position (work position), in which said permanent magnet is located laterally next to the one reaction vessel and exerts a magnetic force on the particles, and with said two permanent magnets of said paired arrangement alternating with each other in taking over the above-mentioned first position or the above-mentioned second position, relative to the reaction vessel positioned between the magnets, and alternating between the said positions at a predetermined velocity and/or for a predetermined duration.

2. The device according to claim 1, wherein the drive unit of the movable permanent magnets is programme-controlled by a device selected from the group consisting of an integrated microprocessor control unit and a computer connected via an interface.

3. The device according to claim 1, wherein at least one of the velocity, the frequency, the number of cycles of the movements of the magnets, the duration of the pause intervals between the movements, the position of said first or other working position in vertical direction, and the sequence in which the permanent magnets take up said positions is predeterminable or controllable by a programme.

4. The device according to claim 1, wherein the two permanent magnets of said paired arrangement are mechanically coupled to each other so that, relative to the reaction vessel, one magnet is located in said first position when the other magnet is located in the said second or other position, and vice versa.

5. The device according to claim 1, wherein the two permanent magnets of said paired arrangement are coupled to each other so that the vertical directions of movement of each magnet of said paired arrangement are opposite to each other.

6. The device according to claim 1, wherein the drive unit of the permanent magnets comprises at least one of electromotors and a pneumatic, hydraulic or electromagnetic drive means.

7. The device according to claim 1, and further comprising a plurality of said pair-wise arranged permanent magnets arranged in a row.

8. The device according to claim 1, wherein said permanent magnets can be brought into an elution position in which one permanent magnet is located at the bottom end of and beside the reaction vessel, and in which said permanent magnet exerts a magnetic force on the particles.

9. The device according to claim 1, wherein said holder is arranged to enable movement in a vertical direction, and can be brought from a lower or starting position to a predeterminable upper position by a drive apparatus, so that said permanent magnet, when located in said working position at said reaction vessel, is positioned at the bottom end of the reaction vessel and is located at said elution position.

10. The device according to claim 1, wherein said drive unit is movably arranged and can be brought from an upper or starting position to a predeterminable lower position by a drive means, so that said permanent magnet, when located in said working position at said reaction vessel, is positioned at the bottom end of the respective reaction vessel, and wherein at least one of the direction, distance, velocity of the movement of the drive unit, or intermediate pause intervals are predeterminable or programmable.

11. The device according to claim 1, wherein said holder is arranged so as to be movable in at least one of a horizontal direction or a vertical direction, and wherein at least one of the direction, distance, velocity of the movement, or the intermediate pause intervals are predeterminable or programmable.

12. The device according to claim 1, and further comprising at least one device selected from the group consisting of at least one device for the sucking-off of liquid from said at least one reaction vessel and at least one pipetting device for dosing defined volumes of liquid to said at least one reaction vessel, each of these operational steps being programme-controllable.

13. A process for treating magnetizable or magnetically attractable particles, which are present in a reaction vessel, in order to resuspend the particles in a liquid to be added thereto, comprising the step of positioning a permanent magnet from a pair of permanent magnets in alternating order at opposite sides of the reaction vessel by alternatively moving said permanent magnets linearly vertically, so that each permanent magnet of a paired arrangement is brought from a first position or starting position, wherein said magnet is located at a distance from a reaction vessel and where said magnet has no influence on said particles, to a second or to another position (a working position), wherein said magnet is located laterally next to the reaction vessel and wherein said magnet exerts a magnetic force on the particles, with the two permanent magnets of said paired arrangement alternating with each other in taking over said first position and said working position relative to the reaction vessel arranged between the magnets.

14. A process for treating magnetizable or magnetically attractable particles, which are present in a reaction vessel, with a liquid, said process comprising the steps of:

adding a predetermined amount of a liquid to a pellet containing magnetic particles;

resuspending the pelletized particles and mixing with the liquid, wherein the resuspending and mixing step further comprises the steps of:

positioning said reaction vessel between two permanent magnets which are arranged in a pair and opposite to each other, said permanent magnets being linearly vertically movable, and alternatively moving said permanent magnets linearly vertically so that each permanent magnet of a paired arrangement is brought from a first position or starting position, wherein said magnet is located at a distance from a reaction vessel and wherein said magnet has no influence on said particles, to a second or to another position (working position), wherein said magnet is located laterally next to the reaction vessel and wherein said magnet exerts a magnetic force on the particles, with the two permanent magnets of said paired arrangement alternating with each other in taking over said first position and said working position relative to the reaction vessel arranged between the magnets, and changing between the said positions at a predeterminable velocity and for predeterminable durations.

15. The process according to claim 14, and further comprising a binding, washing or elution step which uses a liquid selected from the group consisting of a binding liquid, a wash liquid and an elution liquid.

16. The process according to claim 14 wherein the resuspending and mixing step is carried out in such a manner that said reaction vessel is positioned between two vertically movable permanent magnets which are arranged in a pair and opposite to each other, and each permanent magnet of said paired arrangement is alternately brought into an elution position, in which said magnet is located laterally next to and at the bottom end of the reaction vessel, and in which said magnet exerts a magnetic force on the particles.

17. The process according to claim 16, wherein said permanent magnet is brought to said elution position by moving the reaction vessel or reaction vessel holder carrying the reaction vessel in vertical direction from a lower or starting position to a predeterminable upper position, relative to the working position of the permanent magnet; and moving said starting position of said pair of permanent magnets to a predeterminable lower position, so that said permanent magnet, when located in said work position at said reaction vessel, is positioned at the bottom end of the reaction vessel.

18. The process according to claim 14, wherein said movements of the permanent magnets, or of the reaction vessel holder, are carried out automatically.

19. The process according to claim 14, wherein the resuspension step further comprises a dwell time of a predetermined length following each altering of the position of the permanent magnets.

20. The process according to claim 14, wherein said movements of the permanent magnets, or of the reaction vessel holder, are programme-controlled.

21. A process for treating magnetizable or magnetically attractable particles, which are present in a reaction vessel, in order to resuspend the particles in a liquid to be added thereto, comprising the step of positioning a permanent magnet from a pair of permanent magnets in alternating order at opposite sides of the reaction vessel by moving said permanent magnet linearly vertically, so that said permanent magnet is located beside the reaction vessel- concerned and exerts a magnetic force on the particles.

* * * * *